(12) United States Patent
Harris

(10) Patent No.: US 9,775,500 B2
(45) Date of Patent: Oct. 3, 2017

(54) POLARIZING ENDOSCOPY SYSTEM AND METHOD

(71) Applicant: GLOBALMEDIA GROUP, LLC, Scottsdale, AZ (US)

(72) Inventor: Michael D. Harris, Scottsdale, AZ (US)

(73) Assignee: GLOBALMEDIA GROUP, LLC, Scottsdale, AZ (US)

( * ) Notice: Subject to any disclaimer, the term of this patent is extended or adjusted under 35 U.S.C. 154(b) by 540 days.

(21) Appl. No.: 14/548,882

(22) Filed: Nov. 20, 2014

(65) Prior Publication Data

US 2016/0143518 A1    May 26, 2016

(51) Int. Cl.
| | |
|---|---|
| A61B 1/06 | (2006.01) |
| A61B 1/227 | (2006.01) |
| A61B 1/05 | (2006.01) |
| A61B 1/00 | (2006.01) |

(52) U.S. Cl.
CPC ........ *A61B 1/0646* (2013.01); *A61B 1/00096* (2013.01); *A61B 1/00142* (2013.01); *A61B 1/05* (2013.01); *A61B 1/227* (2013.01); *A61B 1/00165* (2013.01)

(58) Field of Classification Search
CPC .............................. A61B 1/0646; A61B 1/227
See application file for complete search history.

(56) References Cited

U.S. PATENT DOCUMENTS

| | | | |
|---|---|---|---|
| 2,194,523 A | 3/1940 | Hans et al. | |
| 3,146,775 A | 9/1964 | Moore et al. | |
| 3,572,905 A | 3/1971 | Schlapp | |
| 3,759,153 A | 9/1973 | Aimo et al. | |
| 5,198,875 A | 3/1993 | Bazin et al. | |
| 6,010,450 A | 1/2000 | Perkins | |
| 6,032,071 A | 2/2000 | Binder | |
| 6,104,887 A | 8/2000 | Hamasaki et al. | |
| 6,106,457 A * | 8/2000 | Perkins .............. | A61B 1/00041 396/312 |

(Continued)

FOREIGN PATENT DOCUMENTS

| | | |
|---|---|---|
| DE | 102012221527 | 6/2014 |
| WO | 0119235 | 3/2001 |

OTHER PUBLICATIONS

International Search Report and Written Opinion dated Feb. 5, 2016 in Application No. PCT/US2015/061946.

(Continued)

*Primary Examiner* — Andrew Yang
(74) *Attorney, Agent, or Firm* — Snell & Wilmer L.L.P.

(57) ABSTRACT

A medical device comprising an instrument head integral to the medical device having a distal portion, a light source internal to the instrument head coupled to a first channel, a first polarizing filter positioned within the first channel of the instrument head, a second polarizing filter positioned within the second channel for receiving reflected light from the light source, the reflected light received through a sensor axially aligned with the second channel is disclosed herein. The second channel may comprise a distal opening. The second channel may be configured to restrict light from entering the second channel other than by the distal opening. The first polarizing filter may be configured to polarize light from the light source.

23 Claims, 8 Drawing Sheets

(56) References Cited

U.S. PATENT DOCUMENTS

| | | |
|---|---|---|
| 6,269,227 B1 | 7/2001 | Hamasaki et al. |
| 6,389,238 B1 | 5/2002 | Suzuki |
| 6,587,711 B1 | 7/2003 | Alfano et al. |
| 7,004,599 B2 | 2/2006 | Mullani |
| 7,167,243 B2 | 1/2007 | Mullani |
| 7,167,244 B2 | 1/2007 | Mullani |
| 8,588,605 B2 | 11/2013 | Harris |
| 8,774,619 B2 | 7/2014 | Harris |
| 2005/0143626 A1 | 6/2005 | Prescott |
| 2009/0189972 A1 | 7/2009 | Harris |
| 2014/0206979 A1 | 7/2014 | Berkner et al. |

OTHER PUBLICATIONS

Notice of Allowance dated Aug. 13, 2013, U.S. Appl. No. 13/246,590.
Office Action dated Feb. 28, 2013, U.S. Appl. No. 13/246,590.
Notice of Allowance dated Feb. 28, 2014, U.S. Appl. No. 14/049,826.
Office Action dated Nov. 6, 2013, U.S. Appl. No. 14/049,826.

* cited by examiner

POLARIZING ENDOSCOPY SYSTEM AND METHOD

FIELD OF THE INVENTION

The present invention relates to a polarizing system and method for medical equipment, and more specifically to a polarizing system and method for an otoscope.

BACKGROUND OF THE INVENTION

In general, light can be described as a transverse electromagnetic wave and thus its interaction with matter can depend on the orientation of the electric field vector. Such phenomena and interaction are called polarization effects. Various optical elements can change the polarization of a light beam. A polarizing filter may be used to select which light beams/rays are viewed by a lens. Linear Polarizing (PL) and Circular Polarizing (PL-CIR) filters may remove unwanted reflections from non-metallic surfaces such as water, glass, etc. In some cases, use of a polarizing filter may also enable colors to become more saturated and appear clearer, with better contrast.

There exists a need for medical equipment configured to polarizes its own light source and reflect the polarized light back into the medical device. There also exists a need for the level of polarization to be adjustably controlled.

BRIEF SUMMARY OF THE INVENTION

The present disclosure recites medical equipment configured to polarizes its own light source and reflect the polarized light back into the medical device. The present disclosure also discloses adjustably controlling the polarization level.

Advantages of the present invention will become more apparent to those skilled in the art from the following description of the embodiments of the disclosure which have been shown and described by way of illustration. As will be realized, the invention is capable of other and different embodiments, and its details are capable of modification in various respects. Accordingly, the drawing(s) and description are to be regarded as illustrative in nature and not as restrictive. Additionally, the measurements disclosed in the drawings are to be regarded as illustrative in nature and not as restrictive.

A medical device comprising an instrument head integral to the medical device having a distal portion, a light source internal to the instrument head coupled to a first channel, a first polarizing filter positioned within the first channel of the instrument head, a second polarizing filter positioned within the second channel for receiving reflected light from the light source, the reflected light received through a sensor axially aligned with the second channel is disclosed herein. The second channel may comprise a distal opening. The second channel may be configured to restrict light from entering the second channel other than by the distal opening. The first polarizing filter may be configured to polarize light from the light source.

An otoscope comprising an instrument head having a distal insertion portion, a first channel, a second channel, a light source inside the instrument head coupled to the first channel, and an optical system housed within the second channel of the instrument head is described herein. The optical system may comprise a plurality of otoscopy lenses. The optical system may comprise a first polarizing filter positioned within the first channel. The first polarizing filter may be configured to polarize light from the light source, and a second polarizing filter may be positioned within the second channel for receiving reflected light from the light source. The reflected light may be received through a sensor axially aligned with the second channel.

According to various embodiments, a method of polarizing light for medical examination is described herein. The method may include producing light from a light source within a first channel of a medical device. The method may include polarizing the light produced from the light source by a first polarizing filter. The method may include transmitting the polarized light from the first channel from a first radial plane. The method may include reflecting the light off a target. The method may include receiving the reflected light into a second channel of the medical device at the first radial plane. The method may include polarizing the reflected light by a second polarizing filter and receiving the polarizing reflected light by a lens.

DETAILED DESCRIPTION

The following descriptions are of exemplary embodiments of the invention only, and are not intended to limit the scope, applicability, or configuration of the invention in any way. Rather, the following description is intended to provide convenient illustrations for implementing different embodiments of the invention. As will become apparent, various changes may be made in the function and arrangement of the elements described in these embodiments without departing from the spirit and scope of the invention. For example, various changes may be made in the design and arrangement of the elements described in the preferred embodiments without departing from the scope of the invention as set forth in the appended claims.

In general, the present disclosure provides a polarizing system for an instrument, such as a medical instrument, and more specifically to a polarizing system comprising a camera that has an integral light source and integral camera lens objective. According to various embodiments, the medical instrument may be any device configured for an endoscopic and/or an endoscopy environment. These may include an otoscope, an anoscope, a proctoscope, a rectoscope, a fiber-scope, and/or the like. Endoscopic environments may include, the gastrointestinal tract, the respiratory tract, the ear, the urinary tract, a reproductive system, and/or normally closed body systems (such as those accessed through incision).

As used herein "endoscopy" is a term used to describe the inspection of at least a part of the inside of the body. Endoscopy may be performed using a flexible or rigid instrument called an endoscope, with a camera and light at one end and a viewing monitor or eyepiece at the other. The endoscope may be introduced through a natural opening, such as the mouth or anus. Images of the inside of the patient's body can be seen on a screen. The endoscopy procedure may be recorded so that personnel may revisit the footage. An endoscopy may be a non-invasive medical procedure used for investigation or diagnosis, biopsies and foreign object retrieval, without the need for invasive surgery.

For example, as described further herein and in accordance with various exemplary embodiments, a system for polarizing light provided by a light source via a first polarizer and further polarizing reflected light by a second polarizer, such that the provided light and the reflected light are each directed through the first and second polarizers is disclosed.

Figure 1:
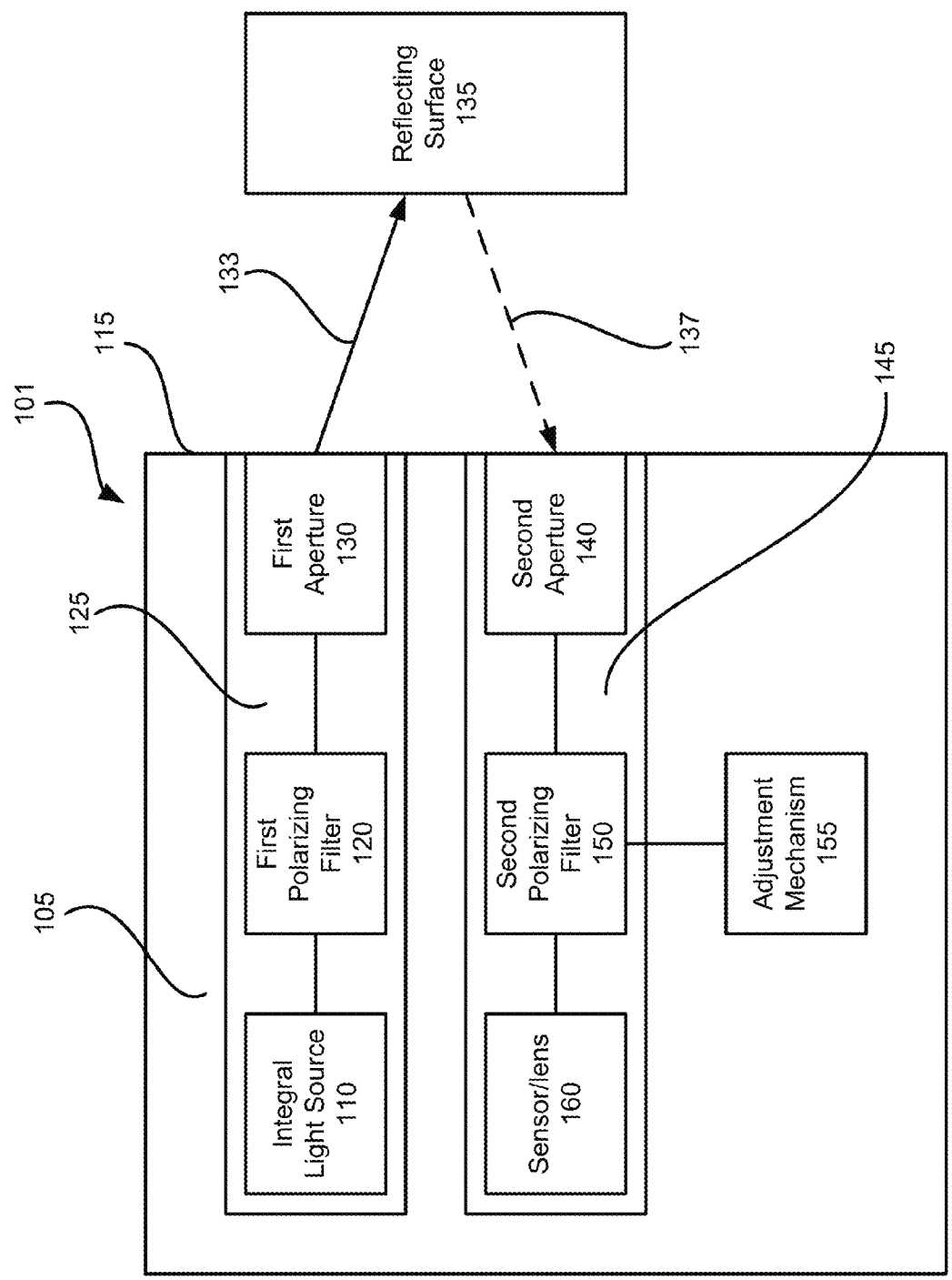
FIG. 1 illustrates a block diagram of an embodiment of a polarizing system and method for medical equipment according to various embodiments.

Referring to FIG. 1, an exemplary embodiment of a polarizing system 101 is shown (in block diagram form). In various embodiments, the polarizing system 101 may comprise an instrument head 105 integral to a medical device. The instrument head 105 may comprise a distal portion 115. The distal portion 115 may be configured for at least partial insertion into an orifice of a body. According to various embodiments, the polarizing system 101 may comprise an integral light source 110. Stated another way, the integral light source 110 may be internal to the instrument head 105. In this way, the light from light source 110 may be insulated from the effects of ambient light prior to interfacing with a first polarizing filter 120. According to various embodiments, a medium for transmitting light rays may be positioned between the light source 110 and the first polarizing filter 120. The medium configured for transmitting light rays may comprise a fiber-optic tube and/or pipe.

First polarizing filter 120 may be housed within instrument head 105, such as within a first channel 125. For instance, the light from light source 110 and/or the first polarizing filter 120 may be housed within first channel 125. The light from light source 110 may pass through first polarizing filter 120 and exit a distal portion 115 via a first aperture 130 of instrument head 105. Stated another way, first aperture 130 may be coupled to and represent an end of first channel 125. First channel 125 may shroud ambient light from passing through first polarizing filter 120. Specifically, first channel 125 may shroud ambient light from passing from a first side of first polarizing filter 120 to a second side of first polarizing filter 120, where the first side of the first polarizing filter 120 is nearer to light source 110 as compared with a second side of first polarizing filter 120.

After passing through first polarizing filter 120, the polarized light generated via light source 110, may exit a distal portion of 115 of instrument head 105, such as via first aperture 130. The polarized light may travel in path 135 to a reflecting surface. The polarized light may illuminate a reflecting surface 135 and/or be reflected off of the reflecting surface 135. The reflecting surface 135 may be an inspection surface. The reflected polarized light may travel in path 137 from reflecting surface to a second aperture 140 housed within instrument head 105, such as within a second channel 145. The reflected polarized light may pass through a second polarizing filter 150. Second polarizing filter 150 and/or channel 145 may be coupled to an adjustment mechanism 155. Adjustment mechanism 155 may be configured to adjust the polarization of second polarizing filter 150. Adjustment mechanism 155 may be configured to adjust the axis of the second polarization filter 150. Stated another way, the second polarizing filter 150 is rotatably adjustable relative to the first polarizing filter 120 to alter the polarity of the received reflected light. For instance, adjustment mechanism 155 may be adjustable via manual and/or electronic manipulation. The reflected polarized light that has passed through second polarizing filter 150 is delivered to a lens and/or sensor 160. According to various embodiments, (not shown) the reflected polarized light that has passed through second polarizing filter 150 is delivered via fiber optics. Lens and/or sensor 160 may be in axial alignment with the second channel 145. Lens and/or sensor 160 may be a digital still camera lens and/or a digital video camera lens. In various embodiments, first channel 125 is isolated from second channel 145. Stated another way, the second channel 145 may be configured to restrict light from entering the second channel 145 other than by the second aperture 140 in the distal portion 115 of instrument head 105. The first channel 125 may be concentric with the second channel 145. The first polarization filter 120 and the second polarizing filter 150 may be linear or circular polarizing filters. A derm hood, such as a specula, may be removably coupled to the instrument head 105 and configured to protect at least the distal portion 115 from contact with foreign bodies.

Figure 2A:
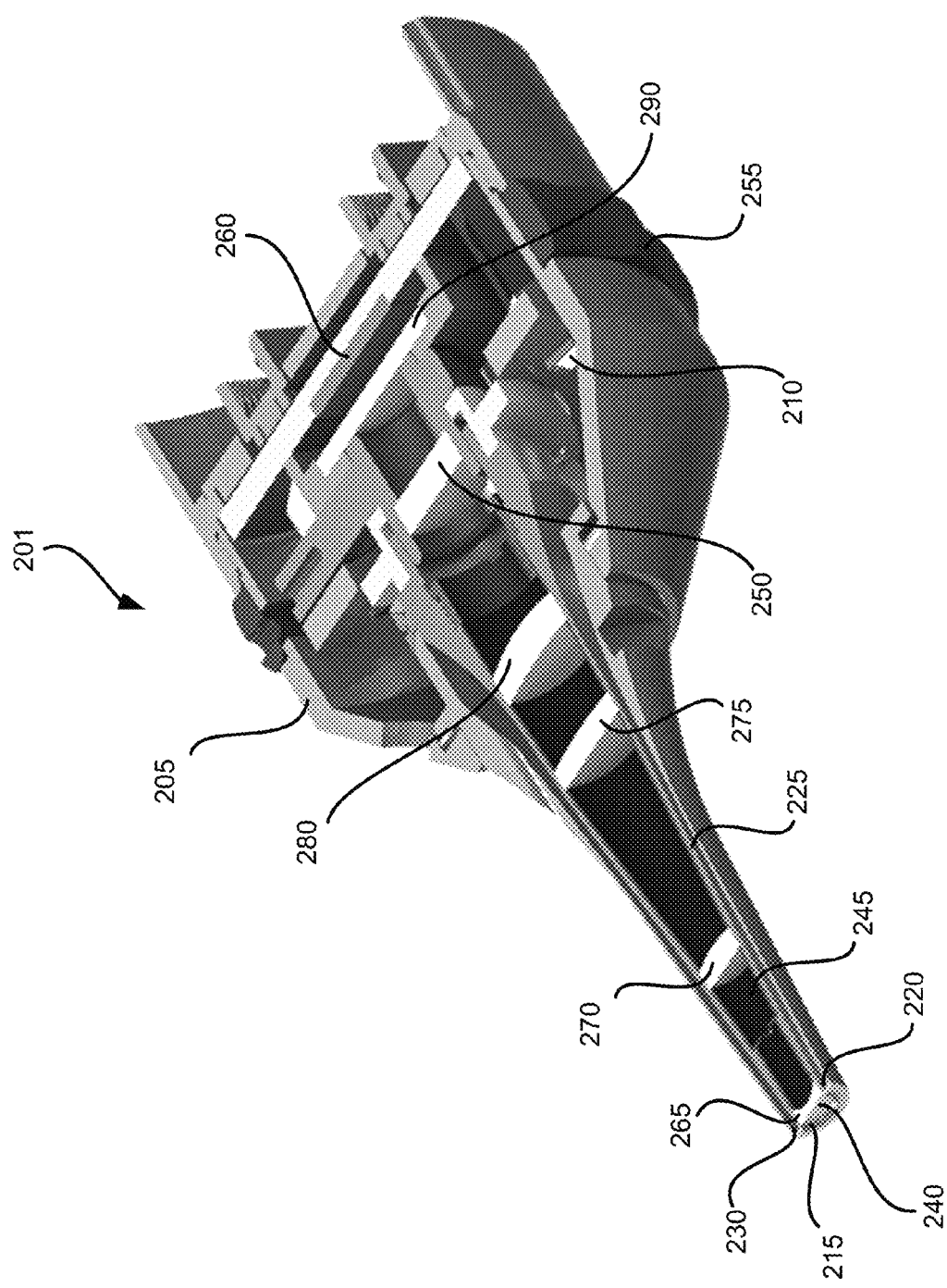
FIG. 2A is an isometric cross-sectional side view of the polarizing system and method for medical equipment of FIG. 1 according to various embodiments.
Figure 2B:
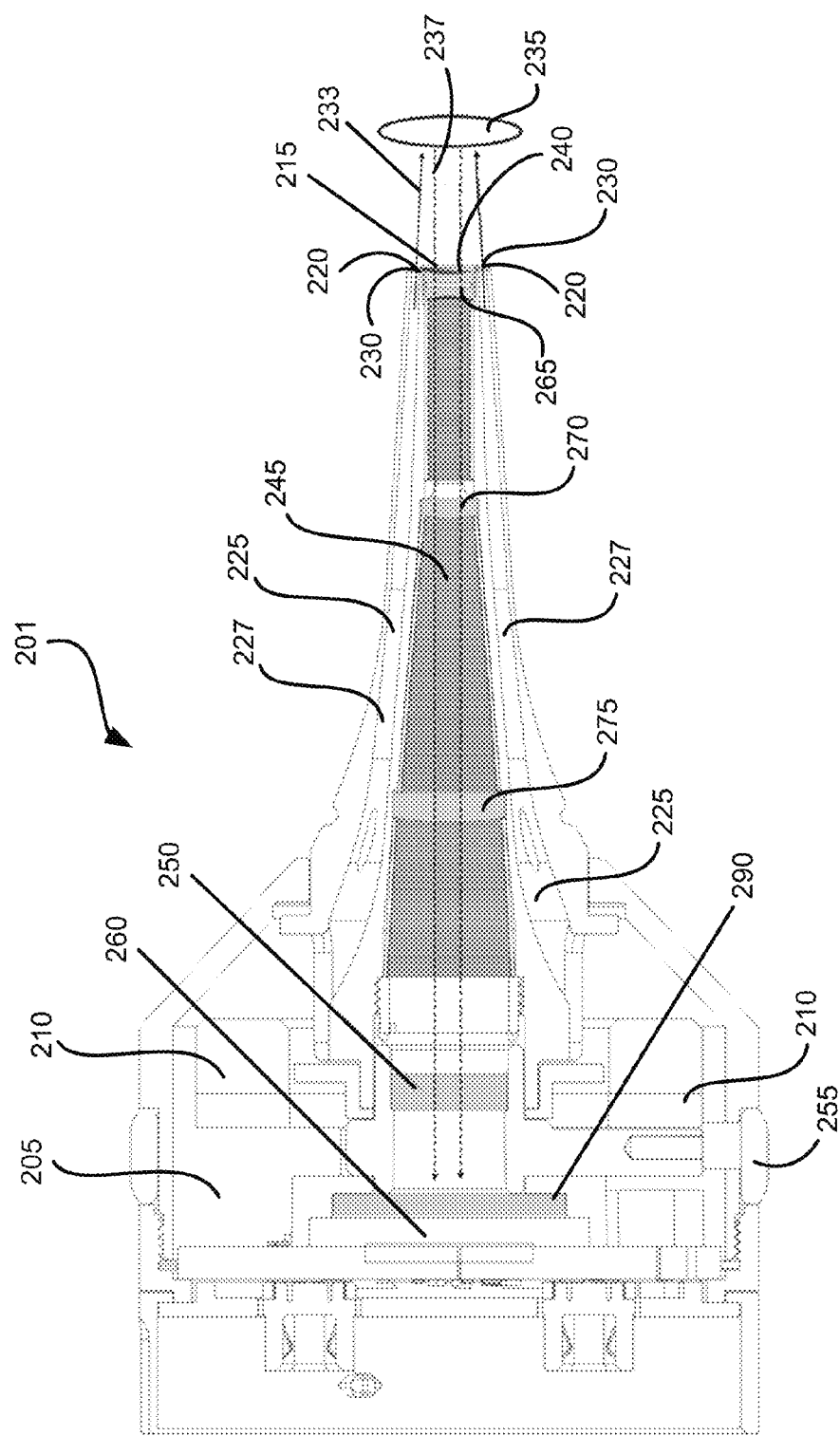
FIG. 2B is a cross-sectional side view of the polarizing system and method for medical equipment along cross section.

In an exemplary embodiment and with reference to FIGS. 2A and 2B an otoscope 201 comprising polarizing system 101 is disclosed. As described herein, the Otoscopy is a category of the endoscopy art specifically directed to the examination of the external canal of the ear and the membranes thereof, namely, the tympanic membrane or eardrum.

With continued reference to FIGS. 2A and 2B, otoscope 201 may comprise an instrument head 205. The instrument head 205 may comprise a distal insertion portion 215. The distal portion 215 may be configured for at least partial insertion into an orifice of a body, such as the ear canal. According to various embodiments, otoscope 201 may comprise an integral light source 210, such as one or more LED light sources. The LED light sources may comprise a color temperature between about 3300 K and 3800 K. Light source 210, (e.g., LED light sources) may be internal to and/or integral to the instrument head 205. Light source 210 may be in communication with a first polarizing filter 220. According to various embodiments, a medium for transmitting light rays may be positioned between the light source 210 and the first polarizing filter 220. The medium configured for transmitting light rays may comprise a fiber-optic tube 227 and/or pipe. This fiber-optic tube 227 and/or pipe may span all or a portion of a channel 225. In this way, the fiber-optic tube 227 may be configured to transmit the light from light source 210 in a non-linear path to first polarizing filter 220 and/or a first aperture 230.

First polarizing filter 220 may be housed within instrument head 205, such as within first channel 225. According to various embodiments, first polarizing filter 220 may comprise a polarized film applied to the end of the fiber-optic tube 227 within channel 225. In this way, the light from light source 210 may be transmitted as near the object under inspection as possible. Stated another way, the light from light source 210 may be transmitted to the distal portion 215 of instrument head 105 within the fiber-optic tube 227 and pass through aperture 215.

According to various embodiments and with continued reference to FIGS. 2A and 2B, the first polarizing filter 220 may be housed within first channel 225. The light from light source 210 may pass through first polarizing filter 220 and exit a distal portion 215 of instrument head 205 via a first aperture 230. First channel 225 may shroud ambient light from passing through first polarizing filter 220. Specifically, first channel 225 may shroud ambient light from passing from a first side of first polarizing filter 220 to a second side of first polarizing filter 220. As mentioned above, the first side of the first polarizing filter 220 may be nearer to light source 210 as compared with a second side of first polarizing filter 220.

After passing through first polarizing filter 220, the polarized light generated via light source 210 may exit a distal portion of 215 of instrument head 205 via first aperture 230. With brief reference to FIG. 3, the polarized light may travel in path 233 to a reflecting surface. The polarized light may be reflected off of a reflecting surface 335, such as an inspection surface of the ear. The reflected polarized light may travel in path 237 from reflecting surface to a second aperture 240 housed within instrument head 205, such as within a second channel 245. The reflected polarized light may pass through a second polarizing filter 250. The reflected polarized light that passes through the second polarizing filter 250 polarizes the light being reflected back from the object under inspection. Also, light that passes through second aperture 240 is polarized by the second polarizing filter 250. Second polarizing filter 250 and/or channel 245 may be coupled to an adjustment mechanism 255. Adjustment mechanism 255 may be configured to adjust the polarization of second polarizing filter 250. Adjustment mechanism 255 may be configured to adjust the axis of the second polarization filter 250. Stated another way, the second polarizing filter 250 is rotatably adjustable relative to the first polarizing filter 220 to alter the polarity of the received reflected light. For instance, adjustment mechanism 255 may be adjustable via manual and/or electronic manipulation. Adjustment mechanism 255 may be a hand control ring configured to rotate the axis of the second polarizing filter 250 and/or lens. The reflected polarized light that has passed through second polarizing filter 250 is delivered to a lens, eyepiece, window and/or sensor 260. Lens, eyepiece, and/or sensor 260 may be in axial alignment with the second channel 245. Lens and/or sensor 260 may be a digital still camera lens and/or a digital video camera lens. In various embodiments, first channel 225 is isolated from second channel 245. Stated another way, the second channel 245 may be configured to restrict light from entering the second channel 245 other than by the second aperture 240 in the distal portion 215 of instrument head 205. The first channel 225 may be concentric with the second channel 245. The first polarization filter 220 and the second polarizing filter 250 may be linear or circular polarizing filters.

The instrument head 205 is configured to provide structural support for at least the various polarizing system 101 elements. Though it may be any suitable shape, in an embodiment, the exterior surface of otoscope 201 is generally conical. In this way, an interior cavity, such as a channel 245 of otoscope 201 gradually increases from the end a distal portion 215 to an opposite end. In this way, the instrument head 205 tapers in diameter from a proximate portion to the insertion distal portion 215. Stated another way, the second channel 245 tapers in diameter from a proximate portion to a distal portion. A distal end of the first channel 225 and an end adjacent to aperture 240 of the second channel 245 may comprise a generally common end plane.

With renewed reference to FIGS. 2A and 2B, otoscope 201 may comprise a plurality of otoscopy lenses, such as lenses 265, 270, 275, 280. The otoscopy lenses 265, 270, 275, 280 may be housed within channel 245. The otoscopy lenses 265, 270, 275, 280 may be in axial alignment with second polarizing filter 250 and/or sensor 260. Otoscope 201 may comprise a filter 290, such as a cut-off filter, (e.g., such as a cut off between about 630 nM and about 695 nM, for instance about an 645 nM cut-off filter.)

According to various embodiments and with continued reference to FIGS. 2A and 2B, the first channel 225 and the second channel 245 may be generally concentric. Additionally, the first polarizing filter 220 may be concentric to and positioned within the same plane as an otoscopy lens of the plurality of otoscopy lenses 265, 270, 275, 280. The first polarizing filter 220 may be concentric to the second channel 245. An outer wall of at least one of the first channel 225 and/or the second channel 245 is configured to block light from the light source from passing through an otoscopy lens of the plurality of otoscopy lenses 265, 270, 275, 280.

Otoscope 201 may comprise surface features to aid in positioning polarizing otoscope 201 and/or the polarizing system 101. For instance, an external surface of otoscope 201 may be marked with one or more surface markings, such as an arrow or line to indicate 0 axis position, to aim otoscope 201 and/or an associated camera. Otoscope 201 may also comprise surface features to aid positioning second polarizing filter 250. For instance, the hand control ring of otoscope 201 may be marked with one or more surface markings such that a user may be able to select and note a preferred polarization setting. For instance, these surface markings may include dashes at regular intervals with associated characters, such as numbers, to indicate degrees from the 0 axis position. Polarizing filters described herein may be any desired polarizing filters. For instance, the polarizing filters described herein may be a linear polarizing filter, a circular polarizing filter, or a reflecting polarizing filter. The linear polarizing filter may be dichroic. In its broadest sense the term dichroism may refer to the selective absorption of one of the two orthogonal components of an incident beam of light. The polarizing filter may be impregnated with a compound which makes the molecules conductive so they absorb light whose electric field is parallel to the molecular chains. The resultant polarizing filter blocks waves with electric fields along the molecular axes, and passes waves with perpendicular electric fields. The output is a beam which is linearly polarized along the preferred axis.

Metering and auto-focus sensors in certain cameras, including virtually all auto-focus single lens reflect cameras, may not work properly with a linear polarizer because the beam splitters used to split off the light for focusing and metering are polarization-dependent. A circular polarizer may include a linear polarizer on the front, which selects one polarization of light while rejecting another, followed by a quarter wave plate, which converts the selected polarization to circularly polarized light inside the camera, which works with most all types of cameras, because mirrors and beamsplitters split circularly polarized light the same way they split unpolarized light.

The first polarizing filter 220 may be oriented in any suitable orientation, such as with the 0 axis of the polarizing filter directed to the top of otoscope 201 (e.g., twelve o'clock). Alternatively, first polarizing filter 220 may be oriented to optimally interact with known/or measured properties of the provided light source 210.

The polarizing filters described herein may be optimized based on the type of light source. For instance, a polarizing filter for white light (about 560 nm) may not be as efficient as for other light sources such as blue (480 nm), green (560 nm), and/or red (660 nm). The polarizing filters described herein may comprise a multi-resistance coating, to help prevent scratches and repel dirt and water. This coating may also reduce flare and ghosting at the filter surface. The polarizing filter may be a neutral polarization filter with weather and/or dust sealing.

The adjustment mechanism 255 may be manually rotated about the center axis of otoscope 201. Stated another way, in an embodiment, second polarizing filter 250 may be rotated with respect to the objective of lens 260. This rotation may allow a user to select a preferable level of polarization. Adjustment mechanism 255 may comprise a surface feature such as a tab or marking to align second polarizing filter 250 in a preferable orientation. The intensity of the reflected light may be adjusted by rotating second polarizing filter 250 via adjustment mechanism 255. Though second polarizing filter 250 and/or adjustment mechanism 255 are depicted as being manually adjusted, it should be appreciated that second polarizing filter 250 and/or adjustment mechanism 255 may be mechanically and/or automatically rotated in response to electrical control signaling from a controller. It should also be appreciated, that in accordance with Brewster's law, at a certain orientation of rotational polarizing filter 250 substantially all light may be absorbed by polarizing filter 250.

Figure 3:
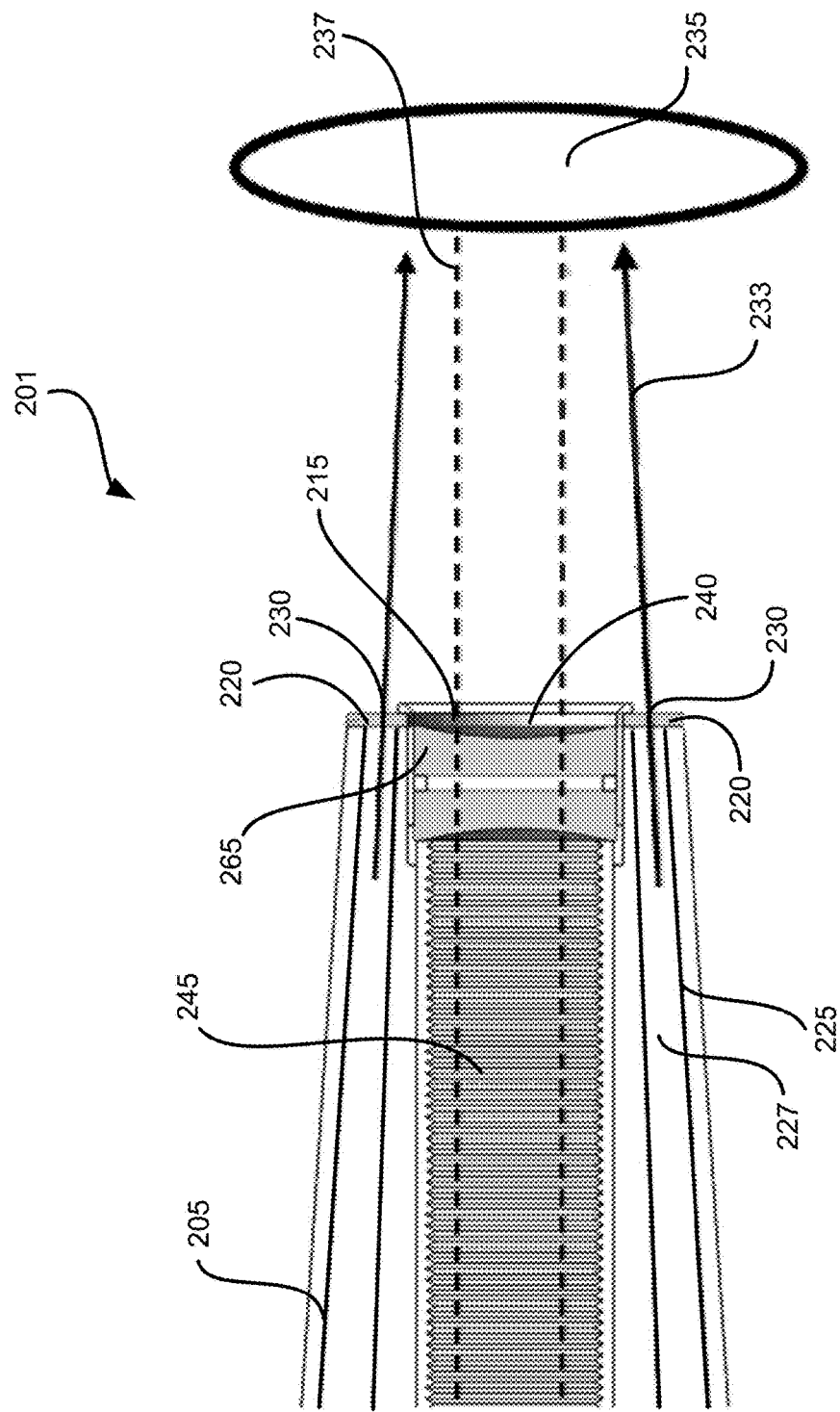
FIG. 3 is a close up side view of a distal portion of the instrument head of the polarizing system and method for medical equipment according to various embodiments.

With reference to FIG. 3, the otoscope 201 may be directed towards an object of interest 235, (in this case, a surface of an ear). Light from light source 210 (with brief reference to FIG. 2B), such as an integral light source, may be communicated down channel 225, such as via fiber-optic tube 227. The light may be directed through the first polarizing filter 220 coupled to and/or in communication with via fiber-optic tube 227. First polarizing filter 220 polarizes the provided light to create controlled beams/rays of light to illuminate a target object with polarized light. Using polarized light, the details of a specimen and/or object being illuminated, including its color, composition and structure which are normally invisible or difficult to discern using non-polarized light may be apparent. The first polarizing filter 220 may be located at the end of channel 225. In this way, polarized light 233 may exit polarizing filter 220 and substantially simultaneously exit otoscope 201. The polarized light 233 illuminates the object of interest 235.

The polarized light 233 is configured to be at least partially reflected from the object of interest 235 and back to otoscope 201. The reflected light 237 is directed through a second aperture 240 which may be collocated with an otoscope lens, such as lens 265. The polarized reflected light 237 is directed down channel 245 towards second polarizing filter 250 and/or sensor 260. With renewed reference to FIG. 2B, the polarized reflected light 237 passes through second polarizing filter 250 and is polarized a preferred amount based on the orientation of adjustment mechanism 255. The polarized reflected light 237 is captured by an integral sensor 260. Optionally, a user may adjust the desired polarization level of the reflected light 237 by rotating second polarizing filter 250 a desired amount by manipulating adjustment mechanism 255. In various embodiments, rotational second polarizing filter 250 may be locked in a preferred orientation via adjustment mechanism 255.

Sensor 260 may comprise a sensor and/or lens of a camera. The camera may be a small, integral, high-resolution examination camera. This camera may be used in the medical and life science fields. Polarization in spectral topography can vastly improve histopathological studies. The camera may be durable, light-weight, easy-to-use, includes a snap-shot capability and is freeze-frame ready. The camera can interface directly into any number of analog or digital video processing devices as needed.

Figure 4:
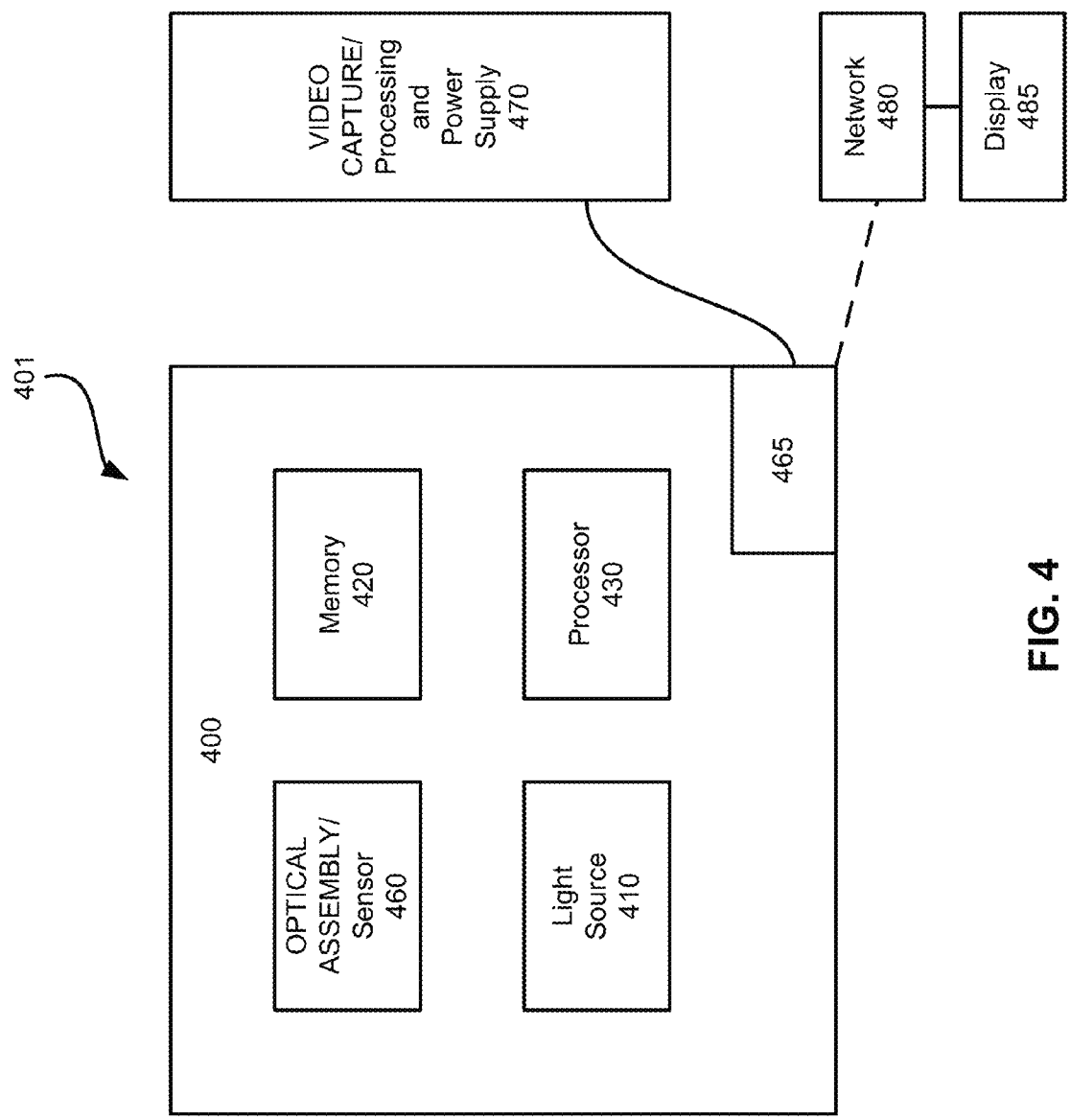
FIG. 4 illustrates a block diagram of a camera integral to a polarizing system and method according to various embodiments.

The block diagram 400 of FIG. 4 includes an examination video camera 401 comprising an optical sensor assembly (e.g., a sensor 460). Sensor 460 may be coupled to a processor 430 and/or a memory 420. The connection may be wired, optical, or wireless. The connection provides data communication and, optionally, power to and from camera 401. Sensor 460 of camera 401 may be axially aligned with one or more otoscope lens of otoscope 201. Camera 401 may be integral to otoscope 201. Light reflected from a reflecting surface 235 is received and processed by sensor 460 and may be transmitted to a video capture and/or processing component 470.

According to various embodiments and with reference to FIG. 4, video camera 401 described herein may be may be coupled to a computing device (e.g., processor 430) and an associated memory 420. Memory 420 may comprise an article of manufacture including a tangible, non-transitory computer-readable storage medium having instructions stored thereon that, in response to execution by a computing device (e.g., processor 430), cause the computing device to perform various methods. The computer-based system may be operatively coupled to a display 485. The computer-based system may be operatively coupled to a receiver 470 and/or transmitter 465 for the transfer of data, such as over a network 480.

Light source 220 or another desired light source can produce visible or non-visible light having any desired wavelength, including, for example, visible colors, ultraviolet light, or infrared light. The light source 220 can produce different wavelengths of light and permit each different wavelength to be used standing alone or in combination with one or more other wavelengths of light. The light source can permit the brightness of the light produced to be adjusted. For example, the light source can comprise 395 nM (UV), 860 nM (NIR), and white LEDs and can operated at several brightness levels such that a health care provider can switch from white light to a "woods" lamp environment at the touch of a control button on the camera 401. The light source, or desired portions thereof, can be turned on and off while camera 401 is utilized to examine a target. In some instances, it may be desirable to depend on the ambient light and to not produce light using a light source mounted in camera 401. In which case reflected light 237 comprises ambient light and/or light from other than the light source 220.

Figure 5:
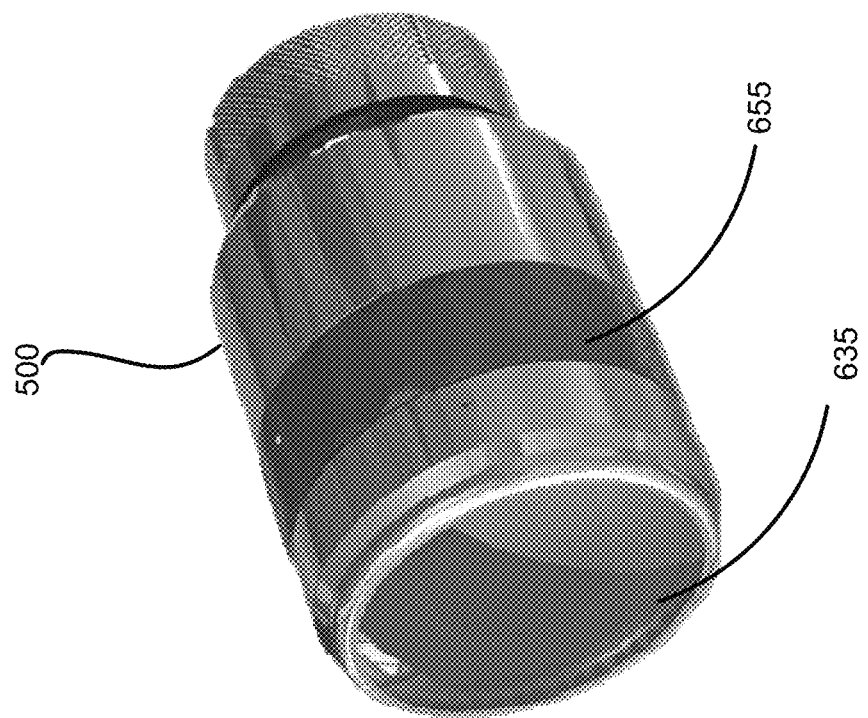
FIG. 5 illustrates an isometric side view of a polarizing system integral to a dermatology apparatus according to various embodiments.
Figure 6:
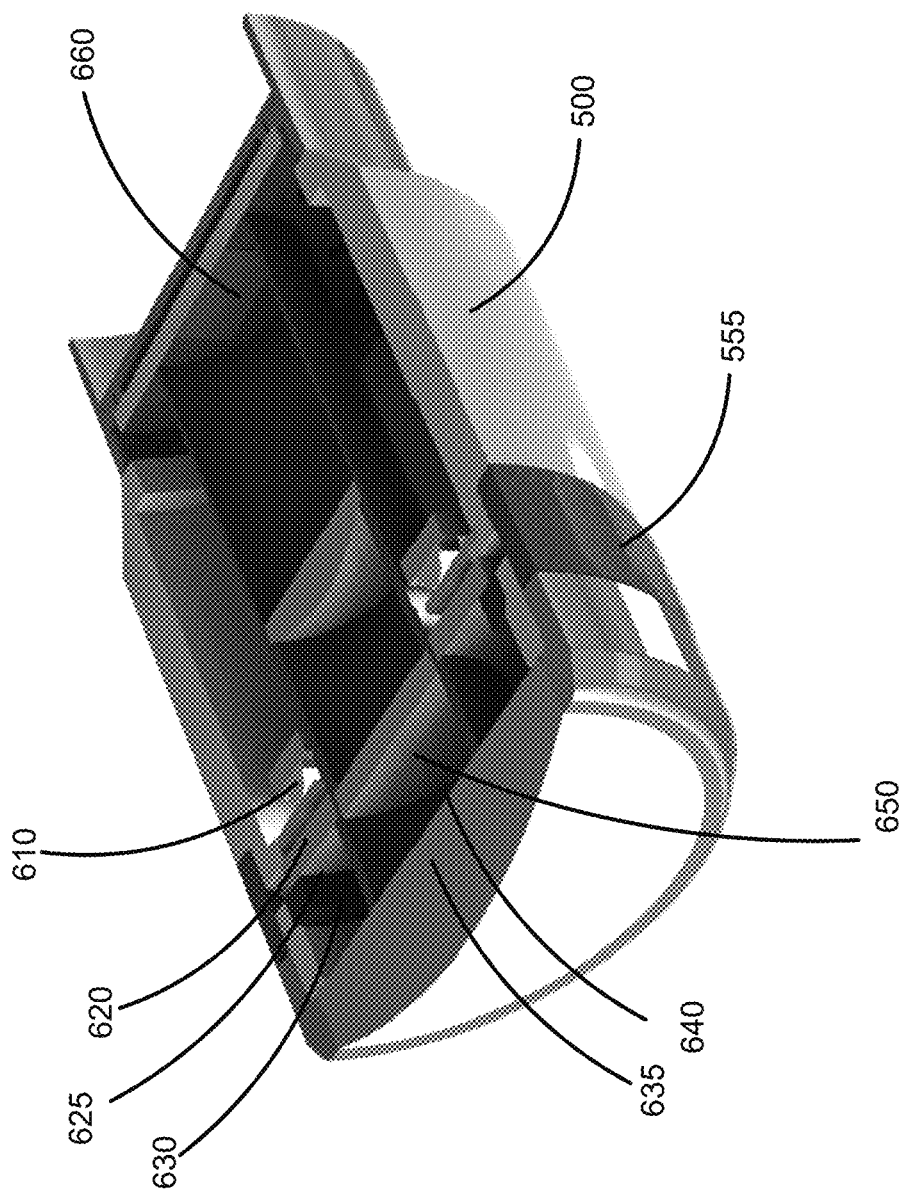
FIG. 6 illustrates an isometric cross-sectional view of the dermatology apparatus of FIG. 5 according to various embodiments.
Figure 7:
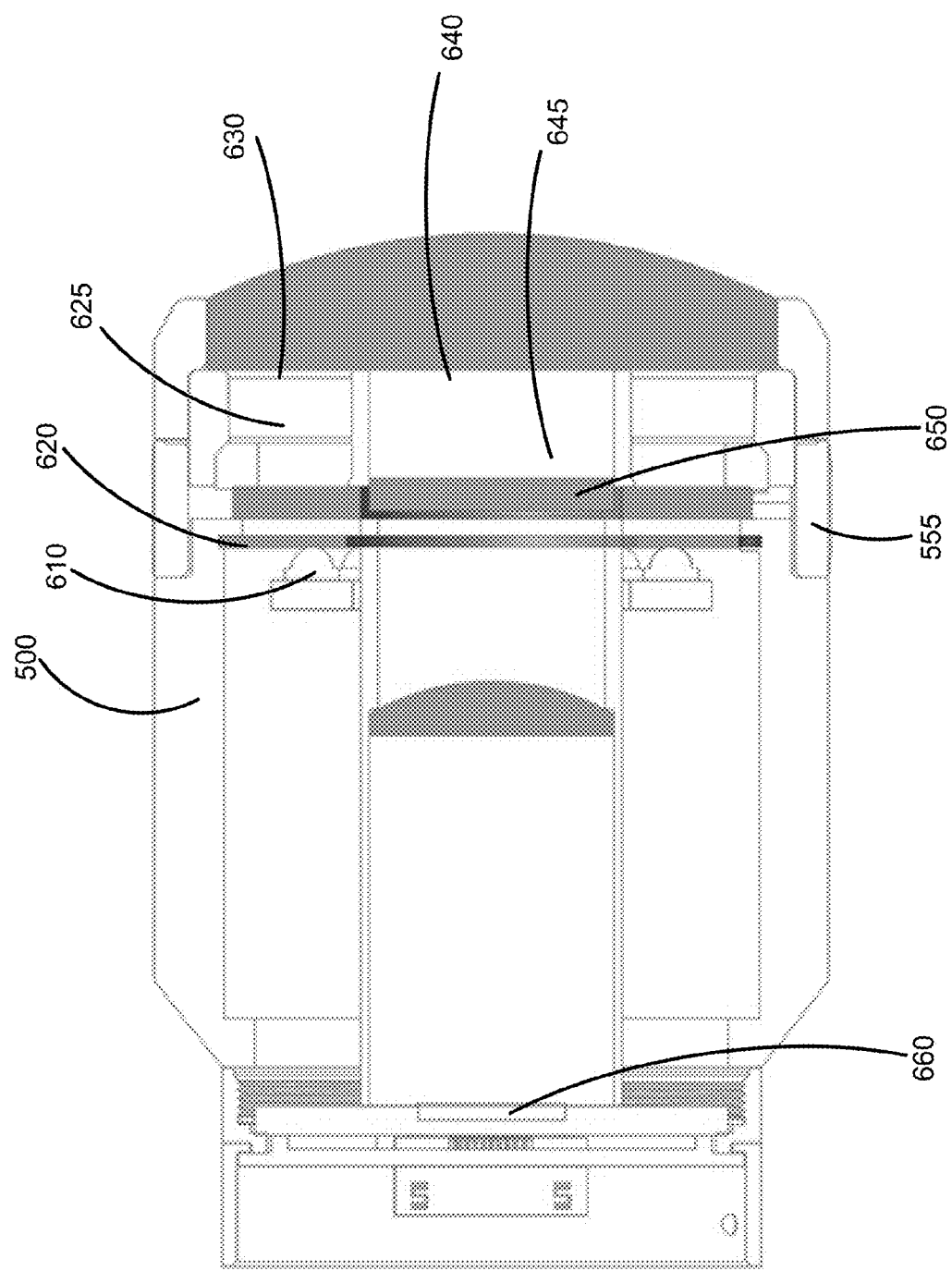
FIG. 7 illustrates a cross-sectional line diagram of the dermatology apparatus of FIGS. 5 and 6 according to various embodiments.

According to various embodiments and with reference to FIGS. 5-7, a dermatology apparatus 500 having an integral polarizing system is disclosed. Dermatology apparatus 500 may comprise an adjustment mechanism 555 which is configured to adjust the polarization of a polarizing filter, such as second polarizing filter 650.

With continued reference to FIGS. 5 through 7 dermatology apparatus 500 may comprise a distal inspection lens 635. The distal inspection lens 635 may be placed near and/or on a portion of a body, such on the skin of a patient. According to various embodiments, dermatology apparatus 500 may comprise an integral light source 610, such as one or more LED light sources. Light source 610, (e.g., LED light sources) may be internal to and/or integral to the dermatology apparatus 500. Light source 610 may be in communication with a first polarizing filter 620. Light passing through first polarizing filter 620 may pass through a portion of a channel 625. Light may pass through channel 625 and exit a first aperture 630. First aperture 630 may be in communication with and/or collated with a portion of distal inspection lens 635, such as the outer perimeter of distal inspection lens 635.

According to various embodiments and with continued reference to FIGS. 5 through 7, the first polarizing filter 620 may be housed within first channel 625. The light from light source 610 may pass through first polarizing filter 620 and exit a distal inspection lens 635 via a first aperture 230. First channel 625 may shroud ambient light from passing through first polarizing filter 620. Specifically, first channel 625 may shroud ambient light from passing from a first side of first polarizing filter 620 to a second side of first polarizing filter 620. As mentioned above, the first side of the first polarizing filter 620 may be nearer to light source 610 as compared with a second side of first polarizing filter 620.

After passing through first polarizing filter 620, the polarized light generated via light source 610 may exit aperture 630. The polarized light may travel in a path to a reflecting surface after exiting distal inspection lens 635 and/or first channel 625. The polarized light may be reflected off of a reflecting surface. The reflected polarized light may travel in path from reflecting surface to a second aperture 640 housed within dermatology apparatus, such as within a second channel 645. Second aperture 640 may be collocated with a portion of inspection lens 635. The reflected polarized light may pass through a second polarizing filter 650. The reflected polarized light that passes through the second polarizing filter 650 polarizes the light being reflected back from the object under inspection. Also, light that passes through second aperture 640 is polarized by the second polarizing filter 650. Second polarizing filter 650 and/or channel 645 may be coupled to an adjustment mechanism 555. Adjustment mechanism 555 may be configured to adjust the polarization of second polarizing filter 650. Adjustment mechanism 555 may be configured to adjust the axis of the second polarization filter 650. Stated another way, the second polarizing filter 650 is rotatably adjustable relative to the first polarizing filter 620 to alter the polarity of the received reflected light. For instance, adjustment mechanism 555 may be adjustable via manual and/or electronic manipulation. Adjustment mechanism 555 may be a hand control ring configured to rotate the axis of the second polarizing filter 650 and/or lens. The reflected polarized light that has passed through second polarizing filter 650 is delivered to a lens, eyepiece, window and/or sensor 660. Lens and/or sensor 660 may be a digital still camera lens and/or a digital video camera lens. In various embodiments, first channel 625 is isolated from second channel 645. Stated another way, the second channel 645 may be configured to restrict light from entering the second channel 645 other than by the second aperture 640. The first channel 625 may be concentric with the second channel 645. The first polarization filter 620 and the second polarizing filter 650 may be linear or circular polarizing filters.

While preferred embodiments of the present invention have been described, it should be understood that the present invention is not so limited and modifications may be made without departing from the present invention. The scope of the present invention is defined by the appended claims, and all devices, process, and methods that come within the meaning of the claims, either literally or by equivalence, are intended to be embraced therein.

The invention claimed is:

1. A medical device comprising:
    an instrument head having a distal insertion portion and a first channel and a second channel;
    a light source inside the instrument head coupled to the first channel;
    an optical system housed within the second channel of the instrument head, said optical system comprising a plurality of otoscopy lenses;
    a first polarizing filter positioned within the first channel, wherein the first polarizing filter is configured to polarize light from the light source; and
    a second polarizing filter positioned within the second channel for receiving reflected light from the light source, the reflected light received through a sensor axially aligned with the second channel;
    wherein the second polarizing filter is rotatably adjustable relative to the first polarizing filter.

2. The medical device of claim 1, wherein the second channel is configured to block ambient light from illuminating the sensor.

3. The medical device of claim 1, wherein the first channel and the second channel are concentric.

4. The medical device of claim 1, further comprising a fiber-optic cable positioned within the first channel between the light source and the first polarizing filter.

5. The medical device of claim 1, wherein the first polarizing filter is concentric to and positioned within the same plane as an otoscopy lens of the plurality of otoscopy lenses.

6. The medical device of claim 1, wherein an outer wall of the second channel is configured to block light from the light source from passing through an otoscopy lens of the plurality of otoscopy lenses.

7. The medical device of claim 1, further comprising a control ring configured to rotatably adjust the second polarizing filter about an axis.

8. The medical device of claim 7, wherein the control ring is configured for manual manipulation.

9. The medical device of claim 1, wherein the instrument head tapers in diameter from a proximate portion to the distal insertion portion.

10. The medical device of claim 1, wherein the second channel tapers in diameter from a proximate portion to a distal portion.

11. The medical device of claim 1, wherein the first polarizing filter is concentric to the second channel.

12. The medical device of claim 1, wherein the first polarizing filter and the second polarizing filter are linear polarizing filters.

13. The medical device of claim 1, wherein the second polarizing filter is configured to alter the polarity of the received reflected light.

14. The medical device of claim 1, wherein the lens is at least one of a digital still camera lens or a digital video camera lens.

15. The medical device of claim 1, wherein a derm hood is removably coupled to the instrument head and configured to protect the distal insertion portion from contact with foreign bodies.

16. The medical device of claim 1, wherein a distal end of the first channel and a distal end of the second channel comprise a common end plane.

17. A medical device comprising:
    a housing having a first channel and a second channel;

a light source coupled to the first channel;

an optical system housed within the second channel, said optical system comprising a plurality of otoscopy lenses;

a first polarizing filter positioned within the first channel, wherein the first polarizing filter is configured to polarize light from the light source; and a second polarizing filter positioned within the second channel for receiving reflected light from the light source, the reflected light received through a sensor axially aligned with the second channel, wherein a distal end of the first channel and a distal end of the second channel comprise a common radial plane;

wherein the second polarizing filter is rotatably adjustable relative to the first polarizing filter.

18. The medical device of claim 17, further comprising a control ring configured to rotatably adjust the second polarizing filter about an axis.

19. The medical device of claim 17, wherein the first polarizing filter is concentric to and positioned within the same plane as an otoscopy lens of the plurality of otoscopy lenses.

20. The medical device of claim 1, wherein the medical device comprises an otoscope.

21. The medical device of claim 1, wherein the medical device comprises a dermatology apparatus.

22. The medical device of claim 1, wherein the medical device comprises a dermascope.

23. A method of polarizing light for medical examination comprising:

producing light from a light source within a first channel of a medical device;

polarizing the light produced from the light source by a first polarizing filter;

transmitting the polarized light from the first channel to a first radial plane;

reflecting the light off a target;

receiving the reflected light into a second channel of the medical device at the first radial plane;

polarizing the reflected light by a rotatably adjustable second polarizing filter; and receiving the polarizing reflected light by a lens.

* * * * *